(12) United States Patent
Grossman et al.

(10) Patent No.: US 11,259,688 B2
(45) Date of Patent: Mar. 1, 2022

(54) DEVICES FOR ASSISTING MANIPULATION OF INPUT MECHANISMS OF MEDICAL INSTRUMENTS

(71) Applicant: Duke University, Durham, NC (US)

(72) Inventors: Hannah Grossman, Durham, NC (US);
Souhaila Noor, Durham, NC (US);
Erin Emmons, Durham, NC (US);
Darin Dufault, Durham, NC (US)

(73) Assignee: Duke University, Durham, NC (US)

( * ) Notice: Subject to any disclaimer, the term of this patent is extended or adjusted under 35 U.S.C. 154(b) by 341 days.

(21) Appl. No.: 16/388,165

(22) Filed: Apr. 18, 2019

(65) Prior Publication Data
US 2019/0320881 A1 Oct. 24, 2019

Related U.S. Application Data (60) Provisional application No. 62/659,326, filed on Apr. 18, 2018.

(51) Int. Cl.
*A61B 1/00* (2006.01)
*A61B 1/005* (2006.01)

(52) U.S. Cl.
CPC ........ *A61B 1/00066* (2013.01); *A61B 1/0052* (2013.01); *A61B 1/00121* (2013.01); *A61B 1/00071* (2013.01)

(58) Field of Classification Search
CPC ............ A61B 1/00066; A61B 1/00121; A61B 1/0052; A61B 1/0014; A61B 1/00137
See application file for complete search history.

(56) References Cited

U.S. PATENT DOCUMENTS

| | | | |
|---|---|---|---|
| 5,667,476 A | 9/1997 | Frassica et al. | |
| 8,092,373 B1 | 1/2012 | Papouras et al. | |
| 8,790,250 B2 | 7/2014 | Petersen et al. | |
| 8,795,160 B2 | 8/2014 | Hosaka et al. | |
| 8,900,132 B2 | 12/2014 | Ishigami et al. | |
| 8,911,362 B2 | 12/2014 | Kaneko | |
| 8,998,800 B2 | 4/2015 | Masaki | |
| 9,146,576 B2* | 9/2015 | Schmieding | ....... A61B 1/00066 |
| 9,658,445 B2 | 5/2017 | Yamamoto et al. | |
| 9,681,795 B2 | 6/2017 | Yasunaga et al. | |
| 9,743,827 B2 | 8/2017 | Yasunaga et al. | |
| 2007/0255104 A1* | 11/2007 | Maruyama | ........... A61B 1/0052 600/148 |
| 2013/0190561 A1 | 7/2013 | Oskin et al. | |
| 2018/0125567 A1* | 5/2018 | Ciccone | .............. A61B 18/149 |
| 2018/0296066 A1* | 10/2018 | Kinoshita | .............. A61B 1/018 |
| 2020/0288944 A1* | 9/2020 | Aswatha Narayana | ..................... A61B 1/0052 |

\* cited by examiner

*Primary Examiner* — Matthew J Kasztejna
(74) *Attorney, Agent, or Firm* — Olive Law Group, PLLC (57) ABSTRACT

Devices for assisting manipulation of input mechanisms of medical instruments are disclosed. According to an aspect, a device includes a body defining an interior shaped to substantially surround and attach to the input mechanism of a medical instrument. The device also includes multiple protrusions attached to the body and each extending in one or more directions towards the medical instrument.

20 Claims, 8 Drawing Sheets

DEVICES FOR ASSISTING MANIPULATION OF INPUT MECHANISMS OF MEDICAL INSTRUMENTS

CROSS REFERENCE TO RELATED APPLICATION

This application claims priority to U.S. Patent Application No. 62/659,326, filed Apr. 18, 2018, and titled DEVICE TO IMPROVE THE ERGONOMICS OF AN ENDOSCOPE HANDLE, the content of which is incorporated herein by reference in its entirety.

TECHNICAL FIELD

The presently disclosed subject matter relates generally to medical instruments. Particularly, the presently disclosed subject matter relates to devices for assisting manipulation of input mechanisms of medical instruments.

BACKGROUND

Endoscopy is a non-surgical procedure that allows doctors to insert and manipulate a long, flexible tube and specialized instrument through orifices in the body to view and operate on internal organs. This procedure is used for diagnosing and treating diseases and conditions of the entire gastrointestinal tract. Endoscopists may use their left hand to manipulate the articulating dials and valves on the endoscope body. Typically, the head of the endoscope is held by the palm, pinky, and ring finger while the middle finger manipulates the air and/or water valve. The index finger is left to manipulate the suction valve while the thumb may strain to articulate the dial set to steer the directions of the endoscope tip. The right hand is used to hold and move the tube portion of the endoscope, as well as apply pressure and torque to move the tube forward as desired.

Endoscopy is an increasingly prevalent procedure in the clinical setting, due to a high incidence of patients with gastrointestinal disorders and a growing geriatric population who especially benefits from minimally invasive procedures. As a result, an endoscopist may perform upwards of 20 endoscopies on a given day. Endoscopists mainly perform colonoscopies and upper endoscopies, assisted by a technician and a nurse. Oftentimes, an endoscopist guides a gastroenterology fellow through these procedures, hence the two users may alternate using the endoscope. Regardless of the procedure or manufacturer, the left-hand controller body is characteristic of virtually every gastrointestinal endoscope.

For many, current endoscopes are not conducive to repeated use due to continuous strain on the thumb and hand during and after performing procedures using the endoscopes. Particularly, the handles of current endoscopes do not account for variability in hand size, thumb mobility, and strength of the hand and fingers. The rigid angulation control knobs (or dials) and stiff grip section (body) have been identified as being sources of thumb discomfort and general taxation on the left hand. Also, another area of difficulty has been identified as the use of the thumb to reach and transition between the vertical dials for physicians with smaller or weaker hands. In view of these difficulties, there is a need for equipment and techniques that improve the ergonomics and manipulation of input mechanisms of endoscopes.

BRIEF DESCRIPTION OF THE DRAWINGS

Having thus described the presently disclosed subject matter in general terms, reference will now be made to the accompanying Drawings, which are not necessarily drawn to scale, and wherein:

SUMMARY

The presently disclosed subject matter includes devices for assisting manipulation of input mechanisms of medical instruments. According to an aspect, a device includes a body defining an interior shaped to substantially surround and attach to the input mechanism of a medical instrument. The device also includes multiple protrusions attached to the body and each extending in one or more directions towards the medical instrument.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

In accordance with embodiments, devices are disclosed for assisting manipulation of input mechanisms of medical instruments. For example, the device may be attached to a deflection knob of an endoscope to improve the ergonomics and manipulation of the knob by an operator of the endoscope. In accordance with embodiments, a device includes a body defining an interior shaped to substantially surround and attach to the deflection knob of an endoscope. The device also includes multiple protrusions attached to the body and each extending in one or more directions towards the endoscope. It is noted that although the devices disclosed herein are applied to endoscope knobs, it should be appreciated that the devices may also be utilized for input mechanisms of other medical instruments or equipment.

As used herein, the term "endoscope" is a medical instrument that can be used to look into the body and to be used in endoscopy procedures. For example, an endoscope may be used to examine internal organs, such as the throat or esophagus. An example endoscope is the Endo 2 with EPK i7010 video processing available from Pentax Medical. This endoscope is representative of a typical endoscope available from various endoscope manufacturers.

Figure 1:
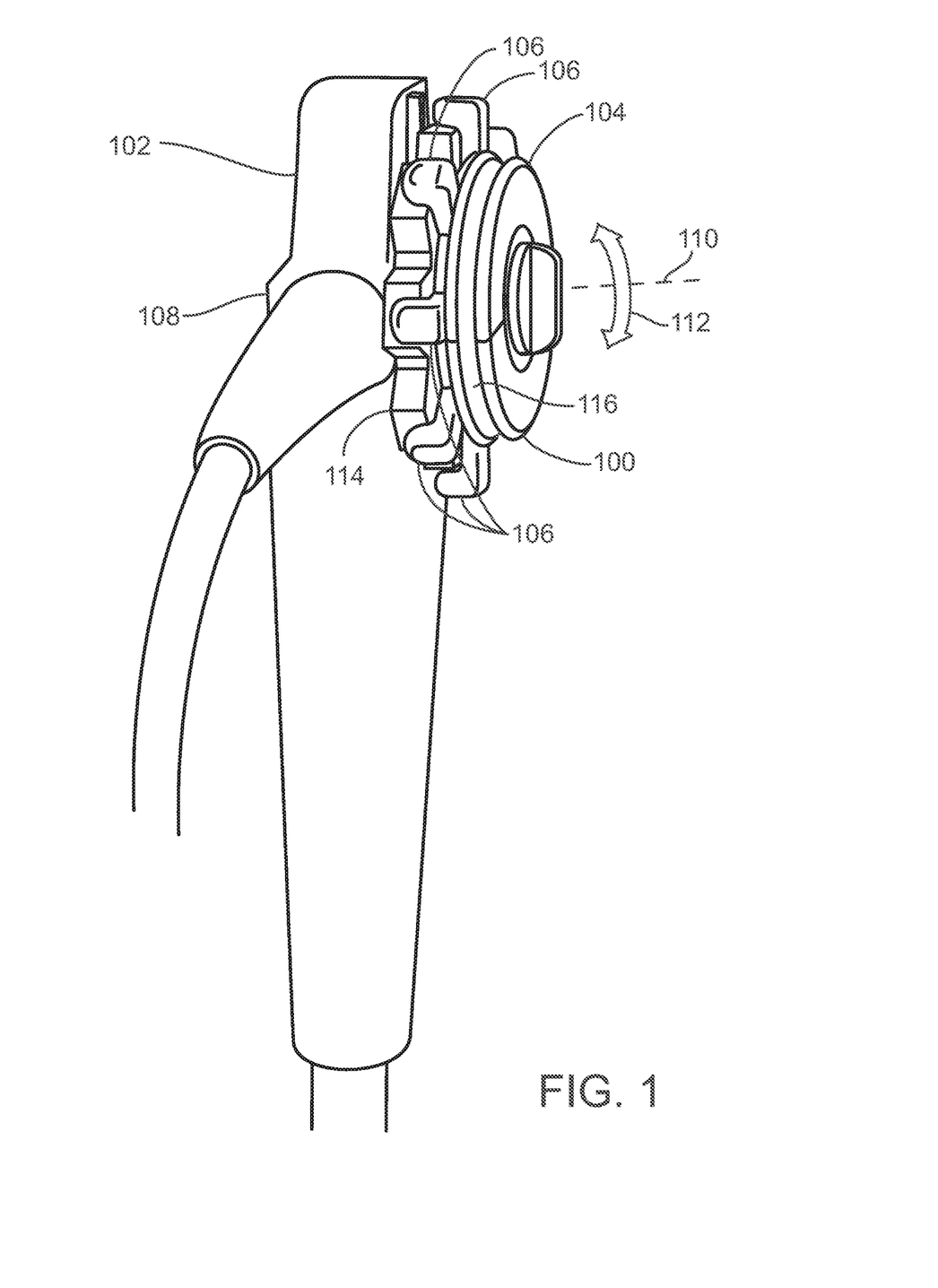
FIG. 1 is a perspective view of a device for assisting manipulation of a deflection knob of an endoscope in accordance with embodiments of the present disclosure.

FIG. 1 illustrates a perspective view of a device 100 for assisting manipulation of a deflection knob of an endoscope 102 in accordance with embodiments of the present disclosure. The device 100 includes a body 104 and multiple protrusions 106 attached to the body 104. The body 104 defines an interior shaped to surround and can attach to the right/left deflection knob (not shown) of the endoscope 102. The interior of the body 104 may be substantially disk-shaped or otherwise suitably shaped and sized to fit onto the right/left deflection knob. The protrusions 106 each extend in directions toward the body 108 of the endoscope 102.

The body 104 may be securely attached to the right/left deflection knob such that rotation about an axis (indicated by broken line 110) in either direction indicated by direction arrows 112 thereby moves the right/left deflection knob in the same direction. Further, the protrusions 106 may be secured to the body 104 such that a predetermined force applied to one or more of the protrusions 106 may cause the body 104 to rotate for rotating the right/left deflection knob. The protrusions 106 extend toward the endoscope body 108 so that an operator's thumb can more easily reach the protrusions 106 to push or pull them for turning the right/left deflection knob. The need reach for the thumb would be greater without the device 100 due to the distance to directly move the right/left deflection knob. By movement of the protrusions 106 to turn the right/left deflection knob, the working tip (not shown) of the endoscope 102 may be moved in the right and left directions as will be understood by those of skill in the art.

In the example of FIG. 1, the device 100 includes parts (described in more detail herein) that are held together by a resilient member 116. In this example, the resilient member 116 is an O-ring that wraps around the body 104 for holding the body 104 together and applying compressive force on the parts of the body 104 such that the body 104 thereby grips onto the right/left deflection knob. It should be noted that although an O-ring is described herein, any other suitable resilient member or component may be used. For example, the resilient member 116 may be any suitable type of rubber material for holding the body 104 together.

Figure 2:
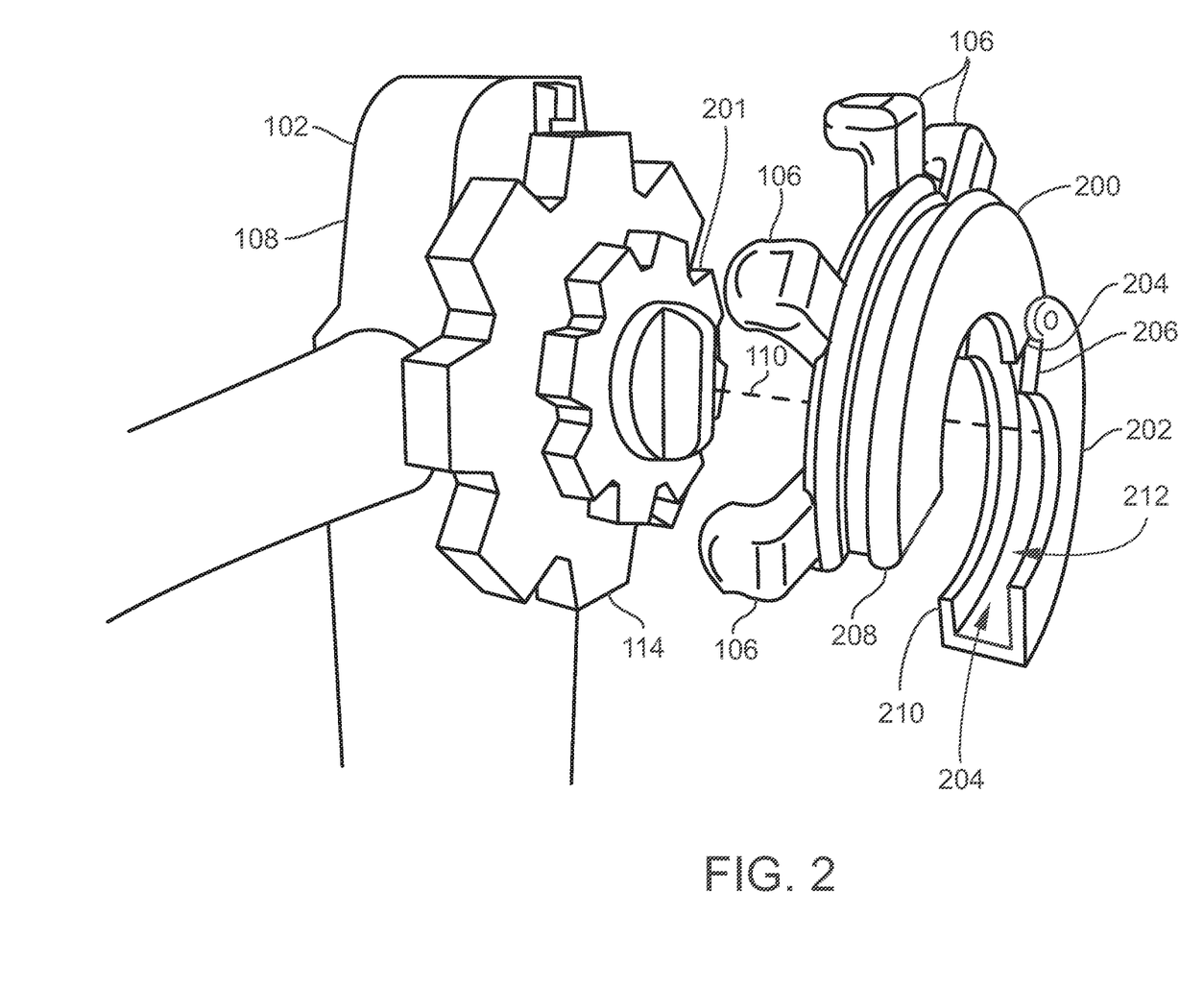
FIG. 2 is a perspective view of the device shown in FIG. 1 in an open position and positioned a distance from the right/left deflection knob of the endoscope.

FIG. 2 illustrates a perspective view of the device 100 shown in FIG. 1 in an open position and positioned a distance from the right/left deflection knob 201 of the endoscope 102. Referring to FIG. 2, the device 100 includes a first part 200 and a second part 202 that are attachable together to define the interior 204 that is shaped to surround and attach to the right/left deflection knob. The first part 200 and the second part 202 have ends 204 and 206, respectively, that are rotatably attached to each other to position the first part 200 and the second part 202 in the open position as shown in FIG. 2. In the open position, ends 208 and 210 of the first part 200 and the second part 202, respectively, are spaced apart from each other. In this way, the device 100 can be clipped or otherwise attached to the right/left deflection knob.

Figure 3:
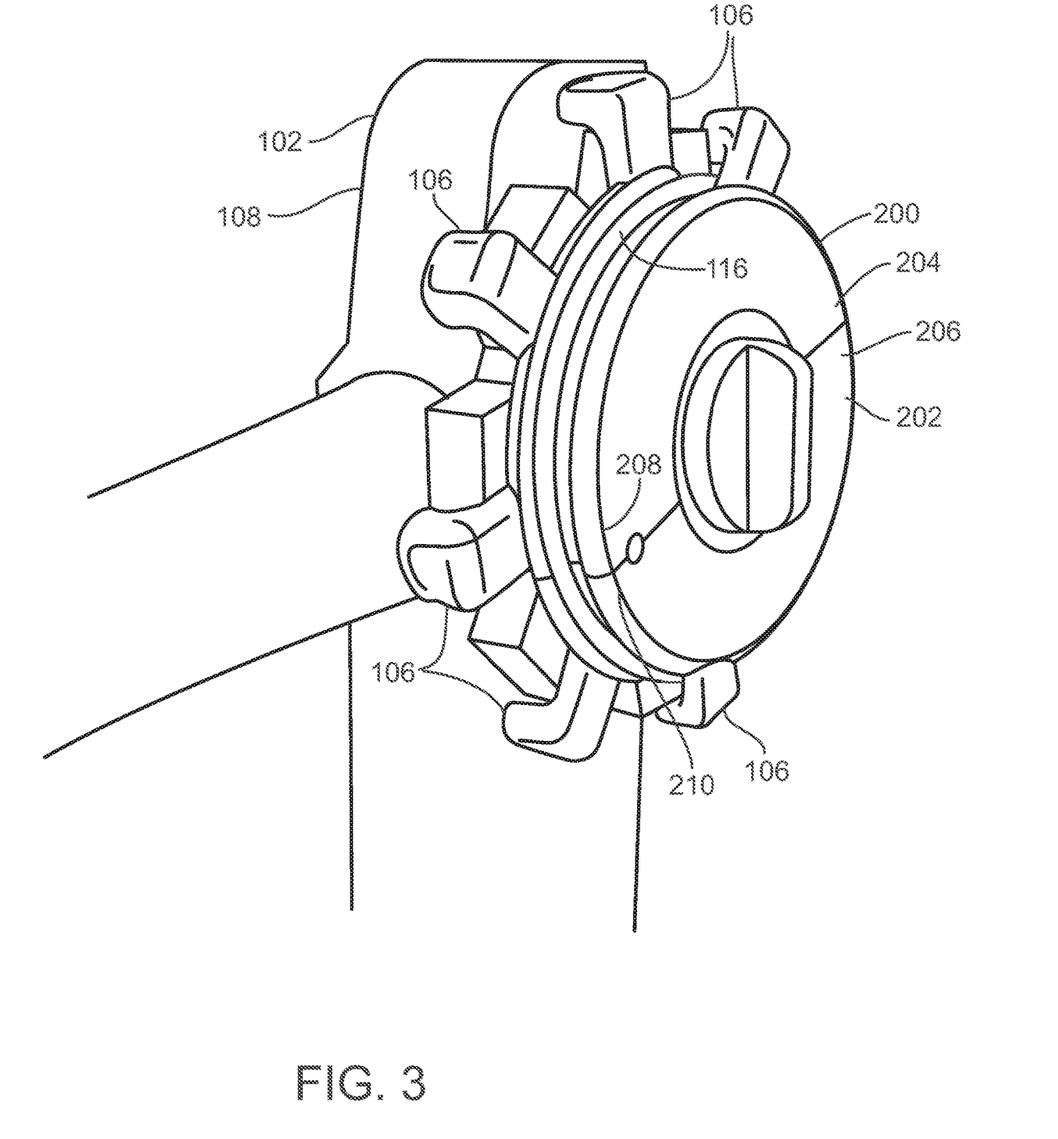
FIG. 3 is a perspective view of the device operably attached the right/left deflection knob of the endoscope and in a closed position.

FIG. 3 illustrates a perspective view of the device 100 operably attached the right/left deflection knob of the endoscope 102 and in a closed position. In this example, the resilient member 116 holds the parts 200 and 202 together in the closed position. In another example, ends 208 and 210 can contact and attached to each other for securing the device 100 to the right/left deflection knob by another suitable mechanism. When the ends 208 and 210 are attached together and the device 100 is attached to the right/left deflection knob as shown in FIG. 1, the first part 200 and the second part 202 can apply a compression force to the right/left deflection knob to securely attach the device 100 to the right/left deflection knob. In the closed position, the parts 200 and 202 define an opening (generally indicated in the space 212 shown in FIG. 2) shaped to surround a portion of the right/left deflection knob. The resilient member 116 (an O-ring in this example) holds the parts 200 and 202 in position as shown in FIG. 3.

The device 100 either entirely or partly may be made of any suitable rigid or semi-rigid material. For example, the body 102 and protrusions 106 may be made of acrylonitrile butadiene styrene (ABS), polylactic acid (PLA), high impact polystyrene (HIPS), nylon, the like, or any other suitable material.

Now with reference again to FIG. 1, the protrusions 106 each have a curved shape that extend away from the body 102. More particularly, the protrusions 106 each extend from their point of attachment to the body 102 outward from the axis 110. From there, the protrusions 106 extend away from the body 102 and to the endoscope body 108. In this example, there are 8 protrusions 106, but it should be understood that there may alternatively be any other suitable number. Also, the protrusions 106 are evenly spaced apart, but may alternatively be spaced apart by any suitable distance. The protrusions 106 may have a length between about 0.3 inches and about 0.4 inches or any other suitable length.

In accordance with embodiments, the endoscope 102 includes an up/down deflection knob 114 as shown in FIG. 1. Knob 114 is placed closer to the endoscope body 108. Knob 114 also rotates about the axis 110 and in a plane perpendicular to the axis 110. The protrusions 106 extend into this plane and are spaced apart from the knob 114 such that they do not interfere with the operation of knob 114. In addition, the protrusions 106 are spaced apart such that the operator's fingers can manipulate the knob 114.

Figure 4:
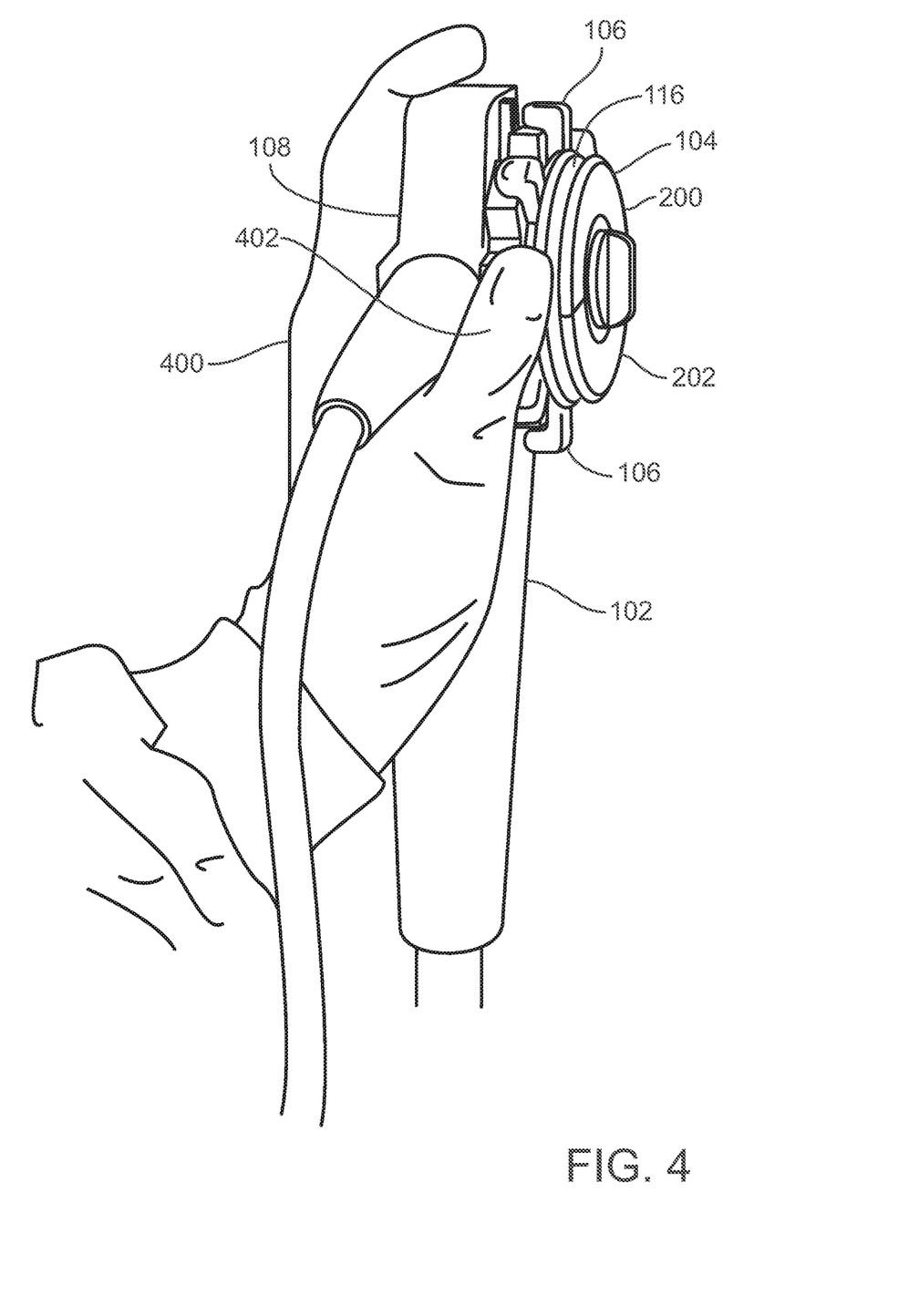
FIG. 4 is a perspective view of the device attached to the endoscope and a user's hand holding the endoscope in accordance with embodiments of the present disclosure.

FIG. 4 illustrates a perspective view of the device 100 attached to the endoscope 102 and a user's hand 400 holding the endoscope 102 in accordance with embodiments of the present disclosure. Referring to FIG. 4, the user may turn the device 100 with her or his thumb 402 for moving the right/left deflection knob as disclosed herein.

Figure 5:
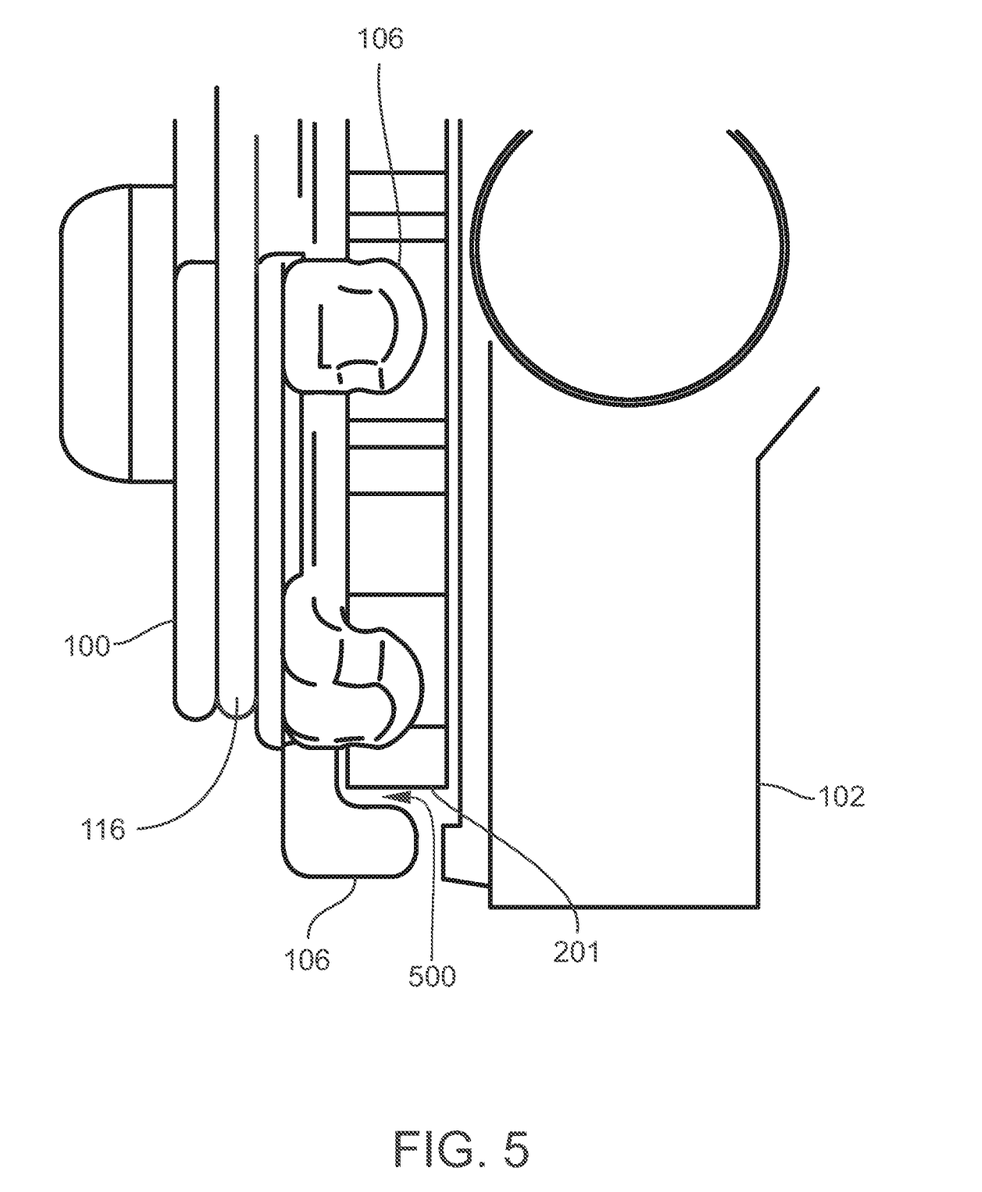
FIG. 5 is a zoomed-in, front view of the device shown in FIGS. 1 and 2 attached to the endoscope.

FIG. 5 illustrates a zoomed-in, front view of the device 100 attached to the endoscope 102. Particularly, FIG. 5 depicts a zoomed-in view of a lower portion of the device 100 to show a space (indicated by arrow 500) between a protrusion 106 of the device 100 and the up/down deflection knob 114 of the endoscope 102. This spacing 500 is provided such that the rotation of the device 100 does not interfere with the up/down deflection knob 114 of the endoscope 102.

Figure 6A:
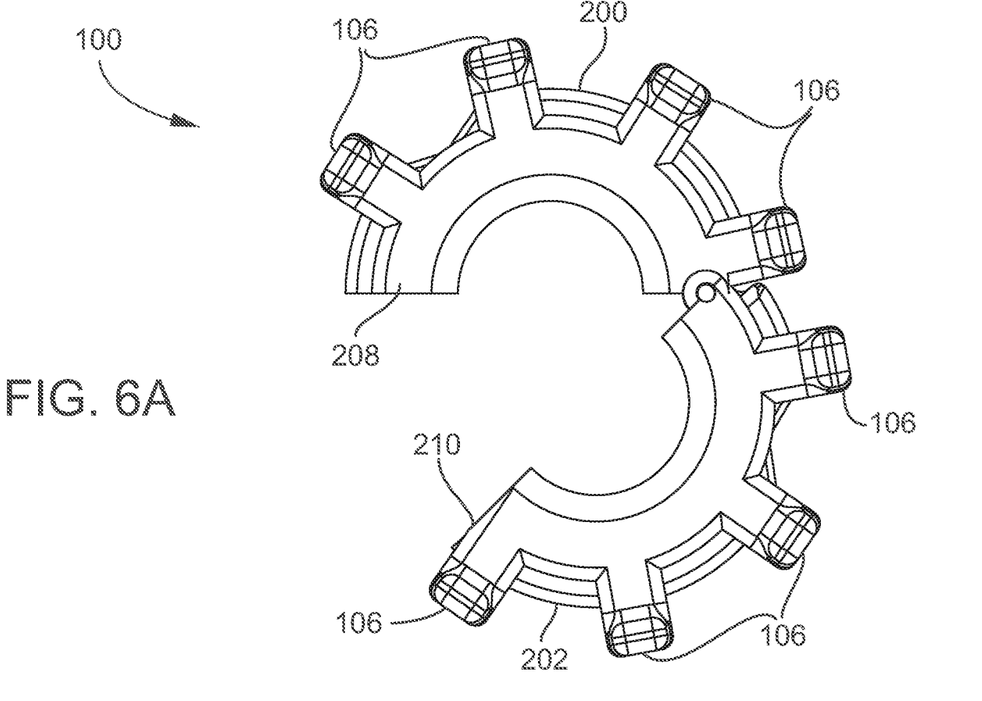
FIGS. 6A and 6B are top perspective views of the device in an open position and a closed position, respectively, in accordance with other embodiments of the present disclosure.
Figure 6B:
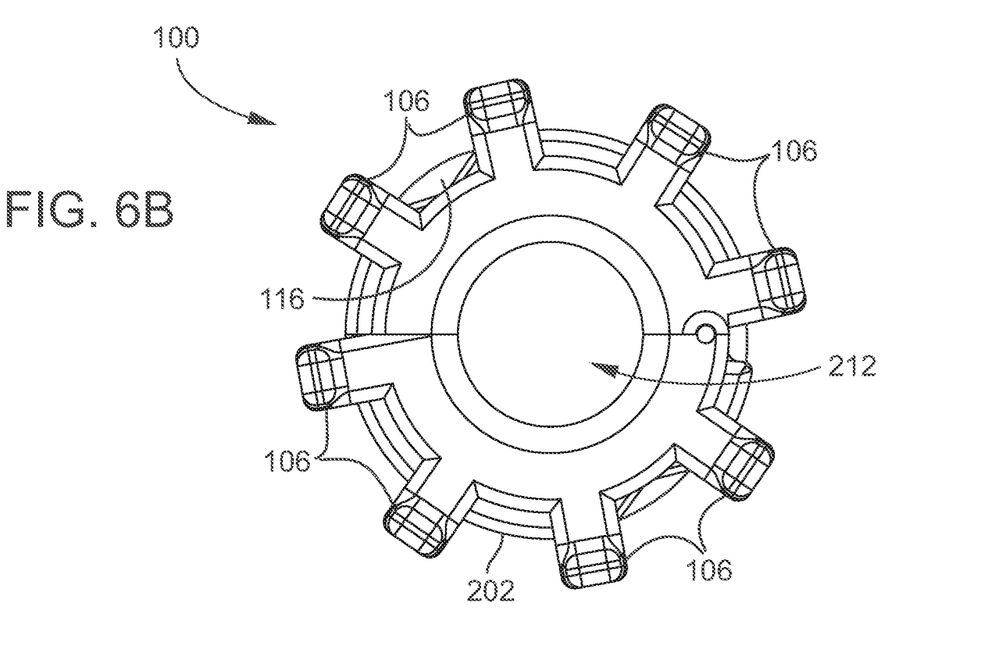

FIGS. 6A and 6B illustrate top perspective views of the device 100 in an open position and a closed position, respectively, in accordance with other embodiments of the present disclosure. In the open position shown in FIG. 6B, the parts 200 and 202 form the opening 212.

Figure 7A:
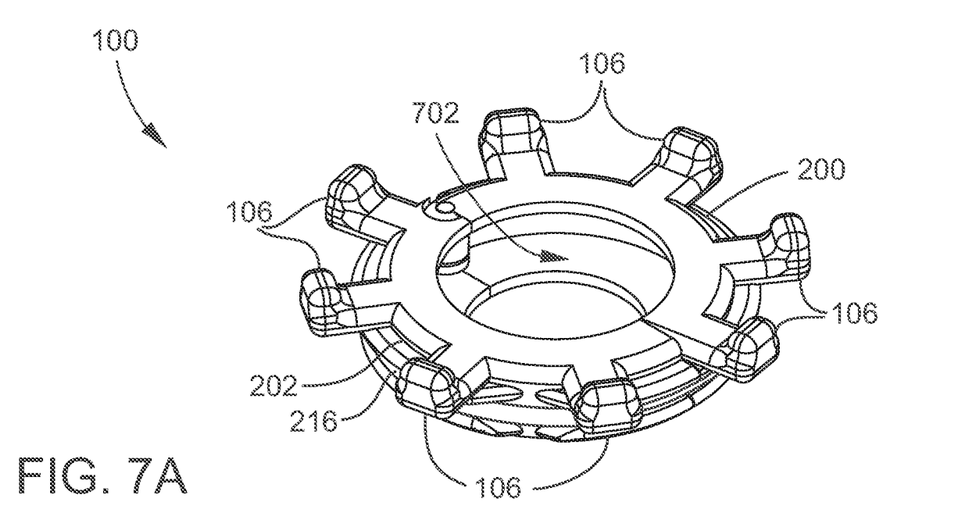
FIGS. 7A and 7B are top perspective views of the device in a closed position and an open position, respectively.
Figure 7B:
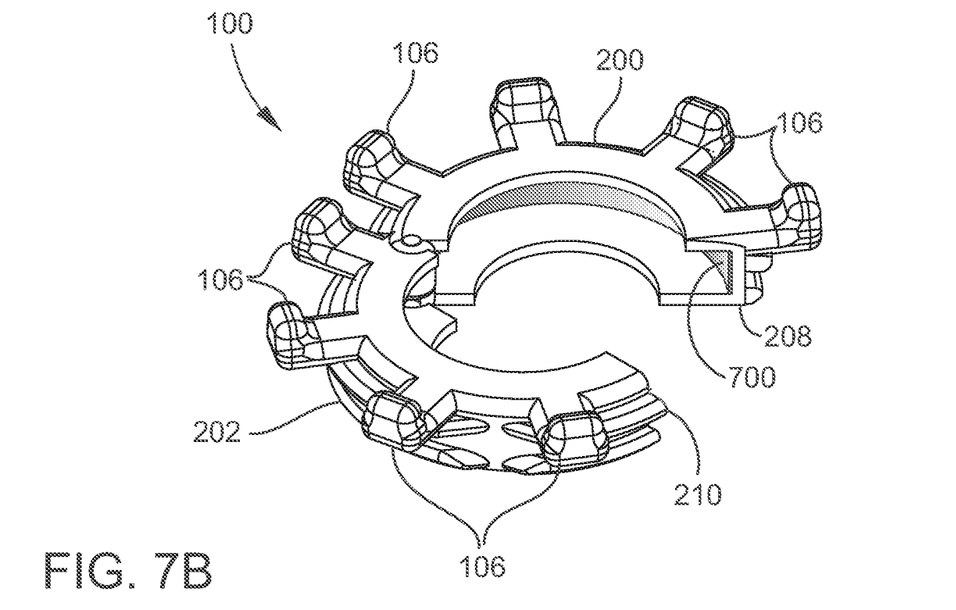
Figure 8A:
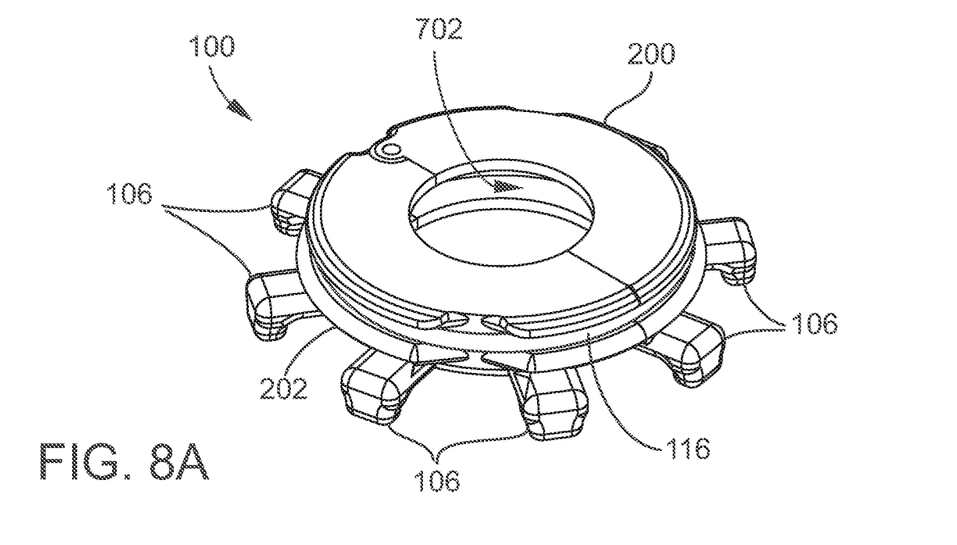
FIGS. 8A and 8B are bottom perspective views of the device in a closed position and an open position, respectively.
Figure 8B:
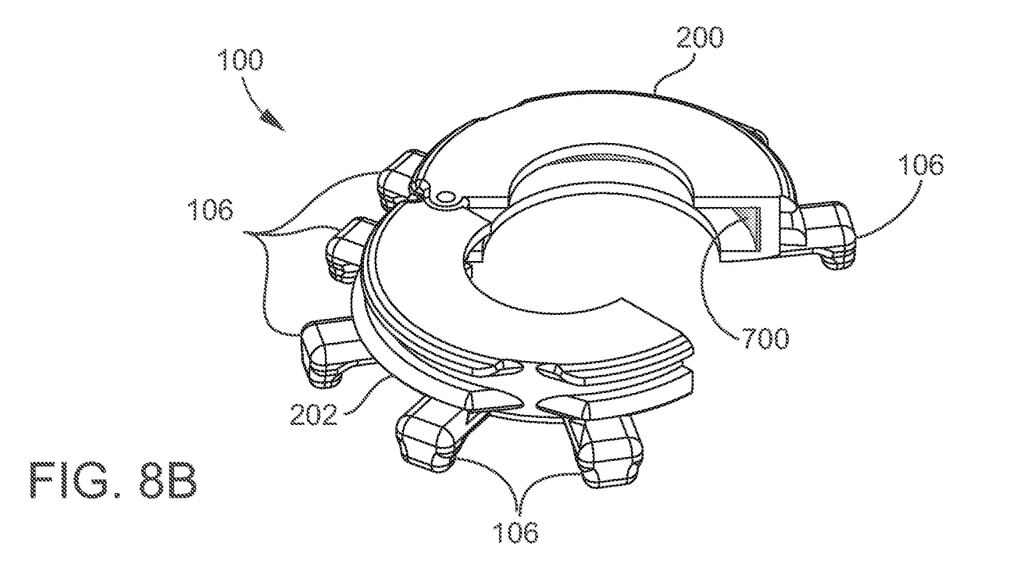

FIGS. 7A and 7B illustrate top perspective views of the device 100 in a closed position and an open position, respectively. In accordance with embodiments, the device 100 may include a gasket 700 positioned between the first part 200 and the second part 202 for being compressed towards the right/left deflection knob when the body 104 is attached to the right/left deflection knob. In an example, the gasket 700 is a band of rubber material, although any suitable type of gasket of any suitable type of material may be used. FIGS. 8A and 8B illustrate bottom perspective views of the device 100 in a closed position and an open position, respectively. FIGS. 7A and 8A also provide a view of an interior space 703 defined when the parts 200 and 202 are in the closed position.

In accordance with embodiments, ends 208 and 210 may be connected or attached to each other by any suitable technique. For example, example mechanism for attaching the ends include, but are not limited to, snap-fit mechanisms, magnets, ball-and-socket mechanism, cantilever mechanisms, and the like.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. A device for assisting manipulation of a control knob of a medical instrument, the device comprising:
   a body comprising a first part and a second part each having a first end and a second end, wherein the first ends are pivotally attached to each other to pivotally position the first part and the second part between an open position and a closed position with respect to each other, wherein in the open position the second ends are spaced apart from each other for receiving or releasing the control knob, and wherein in the closed position the first part and the second part define a substantially disk-shaped interior for holding to an outside portion of the control knob such that movement of the body moves the control knob; and
   a plurality of protrusions supported by the body and each extending in one or more directions away from the body.

2. The device of claim 1, wherein the medical instrument is an endoscope.

3. The device of claim 2, wherein the control knob is a deflection knob.

4. The device of claim 1, wherein the substantially disk-shaped interior defines an interior surface of the body, and wherein the device further comprises a gasket positioned on the interior surface for being compressed towards the outside portion of the control knob when the first part and the second part are in the closed position.

5. The device of claim 1, wherein the first part and the second part are attachable together for defining the interior.

6. The device of claim 5, wherein the first ends of the first part and the second part are rotatably attached to each other.

7. The device of claim 6, wherein the second ends are configured to be securely attached together such that the first part and the second part apply a compression force to the control knob.

8. The device of claim 5, wherein the first part and the second part are configured to be securely attached together such that the first part and the second part apply a compression force to the control knob.

9. The device of claim 5, further comprising a gasket positioned between the first part and the second part for being compressed towards the control knob when the body is attached to the control knob.

10. The device of claim 1, further comprising a resilient member positioned around the body for holding the body together.

11. The device of claim 1, wherein the body is made of material including one of acrylonitrile butadiene styrene (ABS), polylactic acid (PLA), high impact polystyrene (HIPS), and nylon.

12. The device of claim 1, wherein the body defines an opening leading to the interior, wherein the opening is shaped to surround a portion of the control knob.

13. The device of claim 1, wherein the control knob is configured to rotate about an axis for controlling a function of the medical instrument.

14. The device of claim 1, wherein the protrusions each have a curved shape that extend away from the body.

15. The device of claim 1, wherein the number of protrusions is 8.

16. The device of claim 1, wherein the control knob is a first deflection knob of an endoscope,
   wherein the medical instrument includes a second deflection knob adjacent to the first deflection knob, wherein the second deflection knob is rotatable within a plane, and
   wherein the protrusions each extend into the plane and are spaced apart from the second deflection knob.

17. The device of claim 1, wherein the protrusions each have a length between about 0.3 inches and about 0.4 inches.

18. The device of claim 1, wherein the protrusions are made of material including one of acrylonitrile butadiene styrene (ABS) and polylactic acid (PLA).

19. The device of claim 1, wherein the protrusions are secured to the body such that a predetermined force applied to one or more of the protrusions causes the body to move to thereby move the control knob.

20. The device of claim 1, wherein the control knob is pivotable about an axis, and
   wherein the body defines an opening that aligns with the axis when the first part and the second part are in the closed position for holding to the outside portion of the control knob.

\* \* \* \* \*